United States Patent
Groenendaal et al.

(10) Patent No.: US 11,690,529 B2
(45) Date of Patent: Jul. 4, 2023

(54) ELECTRONIC SYSTEM AND METHOD FOR BIOIMPEDANCE SIGNAL ACQUISITION

(71) Applicant: Stichting IMEC Nederland, Eindhoven (NL)

(72) Inventors: Willemijn Groenendaal, Son en Breugel (NL); Seulki Lee, Eindhoven (NL); Ruben De Francisco Martin, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 383 days.

(21) Appl. No.: 16/216,363

(22) Filed: Dec. 11, 2018

(65) Prior Publication Data
US 2019/0175063 A1 Jun. 13, 2019

(30) Foreign Application Priority Data
Dec. 11, 2017 (EP) .................................. 17206469

(51) Int. Cl.
*A61B 5/08* (2006.01)
*A61B 5/00* (2006.01)
(Continued)

(52) U.S. Cl.
CPC .......... *A61B 5/0809* (2013.01); *A61B 5/0535* (2013.01); *A61B 5/1116* (2013.01);
(Continued)

(58) Field of Classification Search
CPC ... A61B 5/053; A61B 5/04002; A61B 5/0535; A61B 5/7221; A61B 5/1116;
(Continued)

(56) References Cited

U.S. PATENT DOCUMENTS 3,677,261 A * 7/1972 Day ..................... H03G 3/3015
600/536
5,063,937 A 11/1991 Ezenwa et al.
(Continued)

FOREIGN PATENT DOCUMENTS

GB 2541947 A * 3/2017 ........... A61B 5/0042
KR 10-2015-0113501 A 10/2015

OTHER PUBLICATIONS (Translated) KR2015 0113501 A ( Korea Advanced Inst Sci & Tech [KR] ; Ko Lon Inc [KR]), Oct. 8, 2015 (Oct. 8, 2015) (Year: 2015).*
(Continued)

*Primary Examiner* — Daniel L Cerioni
*Assistant Examiner* — Jonathan E. Cooper
(74) *Attorney, Agent, or Firm* — McDonnell Boehnen Hulbert & Berghoff LLP

(57) ABSTRACT

An electronic system for bioimpedance signal acquisition, comprises: a current signal injection module configured for generating a current signal to be applied to a subject; a bioimpedance signal measurement module configured for measuring a bioimpedance signal based on a voltage generated by the current signal; a data quality detection module configured for detecting an AC or a DC level of the measured bioimpedance signal and detecting whether the AC or DC level is within or outside an AC reference value range and a DC reference value range, respectively; and a signal adaptation module configured for modifying at least one parameter of the current signal injection module or the bioimpedance signal measurement module based on said detection of the AC or DC level in relation to the AC reference value range and the DC reference value range, respectively.

14 Claims, 8 Drawing Sheets

(51) Int. Cl.
*A61B 5/24* (2021.01)
*A61B 5/0535* (2021.01)
*A61B 5/11* (2006.01)

(52) U.S. Cl.
CPC .......... *A61B 5/2415* (2021.01); *A61B 5/7221* (2013.01); *A61B 5/7271* (2013.01)

(58) Field of Classification Search
CPC ... A61B 5/7228; A61B 5/0809; A61B 5/2415; A61B 5/7271; A61B 5/24; A61H 2230/62; A61M 2230/62; A63B 2230/62
See application file for complete search history.

(56) References Cited

U.S. PATENT DOCUMENTS

| | | | | |
|---|---|---|---|---|
| 6,168,568 B1 * | 1/2001 | Gavriely | ................ | A61B 5/087 600/529 |
| 10,154,460 B1 * | 12/2018 | Miller | ................... | A61B 5/7278 |
| 2008/0177196 A1 * | 7/2008 | Burdick | ............... | A61B 5/4893 600/544 |
| 2010/0105997 A1 * | 4/2010 | Ecker | ................. | A61B 5/02028 600/339 |
| 2010/0113961 A1 * | 5/2010 | Ohlander | .............. | A61B 5/1116 600/547 |
| 2012/0109236 A1 * | 5/2012 | Jacobson | ............ | A61N 1/37217 607/32 |
| 2014/0148656 A1 * | 5/2014 | Zielinski | .............. | A61B 5/0538 600/301 |
| 2014/0257119 A1 * | 9/2014 | LeMay | .................. | A61B 5/304 600/509 |
| 2015/0282768 A1 * | 10/2015 | Luna | .................... | A61B 5/0205 600/386 |
| 2015/0359452 A1 * | 12/2015 | Giovangrandi | ........ | G01G 19/50 600/547 |
| 2016/0015290 A1 | 1/2016 | Kim et al. | | |
| 2016/0074674 A1 * | 3/2016 | Kohli | ................... | A61B 5/0205 600/484 |

OTHER PUBLICATIONS

European Search Report, European Patent Application No. 17206469.3, dated Mar. 19, 2018, 7 pages.

* cited by examiner

ELECTRONIC SYSTEM AND METHOD FOR BIOIMPEDANCE SIGNAL ACQUISITION

CROSS-REFERENCE TO RELATED APPLICATIONS

The present application is a non-provisional patent application claiming priority to European Patent Application No. 17206469.3, filed Dec. 11, 2017, the contents of which are hereby incorporated by reference.

FIELD OF THE DISCLOSURE

The present disclosure relates to a system and a method of bioimpedance signal acquisition. In particular, the present disclosure relates to ensuring that a measured bioimpedance signal is acquired with desirable data quality.

BACKGROUND

Bioimpedance signals are of increasing interest to use for monitoring of health of a subject. A bioimpedance signal may be modulated e.g. by breathing of a subject, and the bioimpedance signal may therefore be used for respiratory monitoring of the subject. This could be used for instance in sleep monitoring applications.

Bioimpedance measurements may be performed with relatively simple equipment causing minimal or at least low inconvenience to the subject on which the bioimpedance measurements are performed. Use of bioimpedance measurements are therefore an especially interesting option in long-term monitoring of health and/or conditions of a subject and/or in monitoring in a home environment (outside a hospital setting).

However, quality of bioimpedance measurements may vary over time. For instance, if the subject moves or changes posture during bioimpedance measurements, the bioimpedance measurement may be affected, which may cause a decay in signal quality or may cause saturation of the acquired signal preventing measurement of bioimpedance. Such variations in signal quality may be particularly occurring in long-term monitoring applications, such as in sleep monitoring.

To prevent saturation, bioimpedance measurements may be based on an injected current having a small amplitude. Thus, the risk of saturation of the bioimpedance signal may be very low. However, it may be difficult to extract information from a detected bioimpedance signal as a signal-to-noise ratio may be low.

SUMMARY

This disclosure relates to a system and method for bioimpedance signal acquisition, allowing acquiring a bioimpedance signal with high quality even in varying acquisition conditions.

According to a first aspect, there is provided an electronic system for bioimpedance signal acquisition, comprising: a current signal injection module configured for generating a current signal that is to be applied to a subject; a bioimpedance signal measurement module configured for measuring a bioimpedance signal based on a voltage generated by the current signal applied to the subject; a data quality detection module configured for detecting an AC and/or a DC level of the measured bioimpedance signal and detecting whether the AC and/or DC level of the measured bioimpedance signal is within or outside an AC reference value range and a DC reference value range, respectively; and a signal adaptation module configured for modifying at least one parameter of the current signal injection module and/or the bioimpedance signal measurement module based on the detection whether the AC and/or DC level of the measured bioimpedance signal is within or outside an AC reference value range and a DC reference value range, respectively.

A decay in signal quality may be identified. Further, based on such identification, settings of bioimpedance signal acquisition may be altered, which may allow the bioimpedance measurement to continuously be acquired with high data quality. Thus, the system allows using adaptive settings for bioimpedance signal acquisition in order to dynamically alter the system to maintain high data quality.

The use of adaptive settings of the bioimpedance signal acquisition may affect AC and/or DC levels of the measured bioimpedance signal. This implies that, in analysis of the measured bioimpedance signal, correction for the change in AC and/or DC level may be necessary in order to make relevant conclusions based on the measured bioimpedance signal. If, for instance, a gain of the measured bioimpedance signal or an amplitude of the generated current signal is changed, this may be corrected for and an absolute value of the measured bioimpedance signal may still be used. However, for other modified parameters, such as a frequency of the generated current signal or a change of electrodes being included in an electrode pair for measuring the bioimpedance signals, the measured bioimpedance signal for different settings may not be compared in absolute terms. However, in many scenarios, an absolute value of the measured bioimpedance signal is not relevant or insignificant. For instance, if a frequency or a relative value is to be extracted, the absolute value of the measured bioimpedance signal may not be relevant. Therefore, the use of adaptive settings of the bioimpedance signal acquisition may for instance be suitable in respiration monitoring, where e.g. a respiration rate is to be determined.

According to one embodiment, the signal adaptation module may be configured for modifying at least one parameter of the current signal injection module. According to another embodiment, the signal adaptation module may be configured for modifying at least one parameter of the bioimpedance signal measurement module. According to yet another embodiment, the signal adaptation module may be configured for modifying at least one parameter of the current signal injection module and at least one parameter of the bioimpedance signal measurement module.

When the signal adaptation module is configured for modifying more than one parameter of the current signal injection module and the bioimpedance signal measurement module, the signal adaptation module may be configured for sequentially modifying the parameters. Thus, a first parameter may first be modified and, if it is determined that signal quality is still not satisfactory after one or more modifications of the first parameter, then a second parameter may be modified.

According to an alternative, the signal adaptation module may be configured to simultaneously change two or more parameters for adjusting settings for bioimpedance signal acquisition.

According to an embodiment, the data quality detection module is configured for detecting an AC level of the measured bioimpedance signal and detecting whether the AC level of the measured bioimpedance signal is within or outside an AC reference value range. The AC reference value range may be set to define acceptable AC levels for high quality acquisition, such that detecting that the AC level of the measure bioimpedance signal is outside the AC reference value range is an indication of a need to modify at least one parameter of the current injection module and/or the bioimpedance signal measurement module. Alternatively, the AC reference value range may be set to define non-acceptable AC levels for high quality acquisition, such that detecting that the AC level of the measured bioimpedance signal is within the AC reference value range is an indication of a need to modify at least one parameter of the current injection module and/or the bioimpedance signal measurement module.

According to an embodiment, the data quality detection module is configured for detecting a DC level of the measured bioimpedance signal and detecting whether the DC level of the measured bioimpedance signal is within or outside a DC reference value range. The DC reference value range may be set to define acceptable DC levels for high quality acquisition, such that detecting that the DC level of the measure bioimpedance signal is outside the DC reference value range is an indication of a need to modify at least one parameter of the current injection module and/or the bioimpedance signal measurement module. Alternatively, the DC reference value range may be set to define non-acceptable DC levels for high quality acquisition, such that detecting that the DC level of the measured bioimpedance signal is within the DC reference value range is an indication of a need to modify at least one parameter of the current injection module and/or the bioimpedance signal measurement module.

According to an embodiment, the data quality detection module is configured for detecting both an AC level of the measured bioimpedance signal and a DC level of the measured bioimpedance signal. The data quality detection module may further be configured for detecting whether the AC level of the measured bioimpedance signal is within or outside an AC reference value range and whether the DC level of the measured bioimpedance signal is within or outside the DC reference value range. Thus, if the data quality detection module detects that either the AC level or the DC level provides an indication of a need to modify at least one parameter of the current injection module and/or the bioimpedance signal measurement module, such modification may be performed by the signal adaptation module. However, modification by the signal adaptation module may alternatively be performed only if both the AC level and the DC level provides an indication of a need to modify at least one parameter of the current injection module and/or the bioimpedance signal measurement module.

According to an embodiment, the AC reference value range and the DC reference value range are predefined value ranges, value ranges defined by performing a system calibration, or value ranges defined by performing a parameter modification by the signal adaptation module.

By the AC reference value range and the DC reference value range being predefined value ranges, the system could be taken into use very quickly and there may not be any need for calibrations or adaptations before the system is used. The predefined value ranges to be used may be determined based on input of set-up of the system and/or the subject on which the system is used. Thus, several predefined value ranges may be set based on characteristics such as body mass index (BMI) of the subject, gender of the subject and/or positioning of current injection and bioimpedance measurement electrodes on the subject's body. Although some input may be given for selecting a predefined value range, there may not be any need of bioimpedance measurements in order to set the predefined value ranges for the AC reference value range and the DC reference value range.

By the AC reference value range and the DC reference value range being defined by performing a system calibration, the system may be set-up to fit the subject on which the system is to be used. Thus, the system may allow personalization to be adapted to a specific subject. This may facilitate the system providing high data quality for each subject on which it is used. The AC reference value range and the DC reference value range being defined by performing a system calibration may be stored in a memory of the system, to allow the calibrated value ranges to be re-used between different sessions of bioimpedance measurements on a subject.

AC reference value range and the DC reference value range may be changed in association with parameter modification. For instance, if a parameter modification process results in that a best possible signal quality is not within desired ranges, the AC reference value range and the DC reference value range may be changed such that the data quality detection module will not constantly trigger a parameter modification. This may allow acquiring bioimpedance signal of a relatively high quality. When it is detected that a higher quality signal may again be acquired, the AC reference value range and the DC reference value range may again be changed for controlling the system to acquire signal quality within desired ranges.

The system may be configured to allow the AC reference value range and the DC reference value range to be defined in one or more ways of the predefined value ranges, value ranges defined by performing a system calibration, and value ranges defined by performing a parameter modification by the signal adaptation module. Thus, depending on the situation, the AC reference value range and the DC reference value range may be defined in different ways.

The AC reference value range may relate to the changes in bioimpedance due to respiration and the DC reference value range may relate to a change in DC level of the bioimpedance signal measurement module.

Thus, the AC reference value range defining acceptable AC levels may be set based on a desired minimum level of the bioimpedance signal to enable acquiring respiration information with a high signal-to-noise ratio. The DC reference value range defining acceptable DC levels may be set based for avoiding saturation, such that bioimpedance measurement is not prevented.

According to an embodiment, the data quality detection module is configured for sending a control signal to the signal adaptation module when the AC and/or DC level of the measured bioimpedance signal is within or outside the reference value range.

According to an embodiment, the data quality detection module is configured for sending a control signal to the signal adaptation module when the AC level of the measured bioimpedance signal is within or outside the reference value range. According to another embodiment, the data quality detection module is configured for sending a control signal to the signal adaptation module when the DC level of the measured bioimpedance signal is within or outside the reference value range. According to yet another embodiment, the data quality detection module is configured for sending a control signal to the signal adaptation module when the AC level and the DC level of the measured bioimpedance signal is within or outside the reference value range.

The sending of a control signal from the data quality detection module may be used as a trigger for the signal adaptation module. This implies that the signal adaptation module need not be active unless a control signal is sent.

According to an embodiment, the control signal indicates to the signal adaptation module when to start and stop modifying the at least one parameter of the current signal injection module and/or the bioimpedance signal measurement module.

The control signal may indicate to the signal adaptation module that parameter modification may be needed so that the signal adaptation module may be triggered to start modifying the at least one parameter of the current signal injection module and/or the bioimpedance signal measurement module.

During parameter modification, the bioimpedance signal measurement module may continuously measure the bioimpedance signal and the data quality detection module may continuously detect the AC and/or DC level and whether the AC and/or DC level is within or outside the AC reference value range and/or the DC reference value range, respectively. If the data quality detection module finds that the AC level and/or DC level is again within an acceptable range (or outside an unacceptable range), the data quality detection module may send the control signal to the signal adaptation module to stop parameter modification.

The parameter modification may be stopped based on signal quality being acceptable. Alternatively or additionally, a maximum time for a parameter modification process may be defined. Thus, during parameter modification, a control whether the maximum time has passed may be performed and, if so, the parameter modification may be stopped, even if the signal quality has not reached an acceptable level. The value(s) of the at least one parameter giving best data quality may then be used, when parameter modification is stopped based on the maximum time having passed.

The signal adaptation module may be configured to receive a control signal based on a maximum time having passed in order to stop parameter modification. However, according to an alternative, the signal adaptation module may itself check whether the maximum time has passed in order to stop parameter modification.

During parameter modification, the bioimpedance signal may not be usable or may be of lower data quality. Thus, the use of a maximum time may ensure that parameter modification does not cause a very long duration of bioimpedance signal of unusable or low quality. Hence, by stopping the parameter modification after the maximum time has passed, a relatively high quality may be acquired based on the value(s) of the at least one parameter giving best data quality. This implies that a period during which analysis of the bioimpedance signal may be prevented, may not be allowed to be too long. If data quality using these value(s) remains below desired levels, a new parameter modification may be started after a period of time, such that data analysis has at least been allowed during a time interval between successive parameter modifications.

According to an embodiment, the data quality detection module is configured for detecting a subjects' respiratory event before sending the control signal to the signal adaptation module to start parameter modification.

A respiratory event, such as hypopnea, shallow breathing and apnea, may cause e.g. an amplitude of an AC level of the bioimpedance signal to be decreased. However, it is not desired that parameter modification is performed due to the respiratory event, as it may require new parameter modification within a short period of time when breathing returns to normal again. By determining whether a respiratory event has occurred/is occurring, parameter modification may be prevented. The respiratory event may be determined based on input from a separate sensor, which may e.g. measure whether any chest movement occurs for detecting apnea.

According to another embodiment, when detecting that the AC and/or DC level of the measured bioimpedance signal is within or outside an AC reference value range and a DC reference value range, respectively, the data quality detection module may monitor data quality for a period of time and, the signal adaptation module is configured for modifying at least one parameter of the current signal injection module and/or the bioimpedance signal measurement module based on detecting that the AC and/or DC level of the measured bioimpedance signal remains within or outside an AC reference value range and a DC reference value range, respectively, during the period of time.

Hence, by waiting a period of time before starting parameter modification, adaptation due to a temporary respiratory event may be avoided. A length of the period of time that data quality is monitored may be set sufficiently long to cover the duration of the respiratory event, but not too long so as to minimize the time duration before parameter modification is started, when parameter modification is actually needed. According to one embodiment, the period of time may be set within a range of 50-180 seconds. In an embodiment, the period of time may be set to 60 seconds. When eventually taking a decision to start parameter modification, the decision may take into account the measured bioimpedance signal during the period of time.

According to an embodiment, the signal adaptation module is configured for modifying an amplitude of the generated current signal, a frequency of the generated current signal, a gain of the measured bioimpedance signal and/or electrodes to be included in an electrode pair for measuring the bioimpedance signal.

The bioimpedance signal may be measured as a voltage between two positions, which voltage is based on the injected current and an impedance between the two positions. Thus, the bioimpedance signal may be linearly dependent on the injected current and on the bioimpedance.

The amplitude of the generated current signal may directly affect an amplitude of the measured bioimpedance signal. Thus, by increasing the amplitude of the generated current signal, an amplitude of the measured bioimpedance signal may also be increased. Similarly, by decreasing the amplitude of the generated current signal, an amplitude of the measured bioimpedance signal may also be decreased.

The impedance of tissue may be dependent on a frequency of a current signal. Thus, by changing the frequency of the current signal, the bioimpedance may be changed, which may cause an amplitude of the measured bioimpedance signal to change. A relation between the magnitude of measured bioimpedance signal and the frequency of the current signal may be expressed by a Cole-Cole plot, forming a semi-circular relation between the resistance and reactance parts of the measured bioimpedance signal at different frequencies. Typically, the resistance value of bioimpedance may decrease with increasing frequency. On the other hand, the reactance value of bioimpedance may decrease or increase with increasing frequency depending on tissue characteristics. Therefore, changing the frequency of the current signal may affect the measured bioimpedance signal, and an effect of a change of the frequency may depend on the positions on a Cole-Cole plot at the initial and new frequency.

The gain of the measured bioimpedance signal used by the bioimpedance signal measurement module may directly affect an amplitude of the measured bioimpedance signal. Thus, by increasing the gain, an amplitude of the measured bioimpedance signal may also be increased. Similarly, by decreasing the gain, an amplitude of the measured bioimpedance signal may also be decreased.

The system may be set up such that a bioimpedance signal may be received from one or more electrode pairs selected from a number of electrodes. Thus, the bioimpedance signal may change depending on which electrodes are active. The signal adaptation module may be configured for modifying which electrodes that are to be included in the electrode pair(s) for measuring the bioimpedance signal. The bioimpedance between two positions may differ depending on the relation between the two positions, such that changing the electrodes to be included in the electrode pair may affect the measured bioimpedance signal.

For instance, a distance between the electrodes may be different, such that depending on which electrodes are selected, the distance in tissue across which the bioimpedance signal is measured may vary. In some setups, the bioimpedance between two positions may be larger if the distance between the positions is larger. Thus, by changing the electrodes to be included in an electrode pair in order to increase the distance between the electrodes, an amplitude of the measured bioimpedance signal may be increased. Similarly, by changing the electrodes to be included in an electrode pair in order to decrease the distance between the electrodes, an amplitude of the measured bioimpedance signal may be decreased.

According to an embodiment, the signal adaptation module is configured for increasing or decreasing a value of the at least one parameter in dependence of a relation between the detected AC level and the AC reference value range and/or the detected DC level and the DC reference value range.

This implies that the adaptation may be performed based on presently used value(s) of the at least one parameter. Thus, if only a minor change in the value(s) of the at least one parameter is necessary, a new setting providing acceptable data quality may be very quickly found. Also, if the AC level and/or the DC level is to be increased, the parameter modification need not consider changes of the at least one parameter which would cause a decrease of the AC level and/or DC level, and vice versa. Hence, an efficient adaptation of the bioimpedance signal acquisition may be achieved.

According to an embodiment, the data quality detection module is configured for monitoring the AC and/or DC level of the measured bioimpedance signal continuously or at predetermined time intervals.

By checking the AC and/or DC level of the measured bioimpedance signal at predetermined intervals, the data quality detection module need not check data quality at every single point in time. Using the predetermined intervals, processing power of the data quality detection module may be saved, while allowing detection of a low data quality relatively quickly. The predetermined intervals may be set based on a likelihood that modifying of at least one parameter may be needed. Thus, the predetermined intervals need not always be the same. Alternatively, the monitoring of the AC and/or DC level may be performed regularly, using a single predetermined interval.

By checking the AC and/or DC level of the measured bioimpedance signal continuously, the data quality detection module may immediately detect if the bioimpedance signal acquisition is providing low data quality.

According to an embodiment, the system further comprises a posture detection module for detecting a posture of a subject and wherein the data quality detection module is configured for monitoring the AC and/or DC level of the measured bioimpedance signal when a posture change is detected by the posture detection module.

Changing of posture may cause changes in data quality of the bioimpedance signal acquisition. Thus, the posture detection module may allow detecting that a subject has changed posture. The input from the posture detection module may thus be used by the data quality detection module as a trigger for monitoring the AC and/or DC level, since the change of posture may be associated with a high likelihood that data quality decreases. By using the posture detection module, the data quality detection module can use large time intervals between monitoring of the AC and/or DC level, as a situation with a high likelihood of requiring parameter modification may be specifically detected by the posture detection module and may cause an extra monitoring of the AC and/or DC level at such point in time.

The posture detection may be made in many different ways. For instance, an accelerometer arranged on the subject may be used for detecting the posture of the subject. As an alternative, a camera monitoring the subject may be used, when the subject is confined to a small space, such as in sleep monitoring. The posture detection module may be configured to receive input from a sensor that may detect information relevant for determining the posture, such as an accelerometer or a camera. Alternatively, the posture detection module may be integrated in the sensor.

According to an embodiment, the signal adaptation module is configured for modifying the at least one parameter of the current signal injection module and/or the bioimpedance signal measurement module further based on posture information from the posture detection module.

The posture information may be associated with suitable value(s) of the at least one parameter. Thus, when a specific posture is detected, such suitable value(s) may be used in parameter modification.

According to an embodiment, settings for the at least one parameter of the current signal injection module and/or the bioimpedance signal measurement module are determined for a subject for different postures of the subject and the determined settings are stored for re-using the at least one parameter as initial settings when a posture change is detected by the posture detection module.

For instance, a system calibration may generate information that can be used for settings in relation to postures. This implies that a personalization of the system is enabled, where the storing of the determined settings allows the system to retrieve updated settings in case of a posture change. As bioimpedance may vary significantly between different persons, such personalization may enable high quality bioimpedance signal acquisition for different subjects.

However, determination of usable settings for different postures need not be performed in a calibration before measurements are initiated. Alternatively, settings for a posture may be determined when the posture is first assumed during measurements. Then, the settings for the posture may be stored for later re-use. The stored determined settings may also continuously be updated based on last used settings for measurements in the posture of the subject.

Thanks to the storing of settings in relation to a posture, the system may quickly retrieve settings when a posture change occurs. This makes the system quickly adapt to a posture change so as to minimize a duration during which data of low quality is acquired.

Personalization of the system need not necessarily include associating settings with different postures. In an embodiment, an initial calibration may be done in a default posture of the subject, in order to determine settings of the at least one parameter, and possibly also value ranges for the AC reference value range and the DC reference value range. The settings may thus be initially used for subsequent bioimpedance signal acquisition. Such initial calibration may be performed for each session of bioimpedance signal acquisition in order to initialize the session. The calibration for a subject may alternatively be stored, such that when a new session of bioimpedance signal acquisition is to be started for the subject, the determined settings may be retrieved.

According to a second aspect, there is provided a wearable device for biosignal acquisition comprising a system for bioimpedance signal acquisition according to any preceding claim.

Effects and features of this second aspect are largely analogous to those described above in connection with the first aspect. Embodiments mentioned in relation to the first aspect are largely compatible with the second aspect.

Thus, the system for bioimpedance signal acquisition may be implemented in a wearable device, which may be worn by a subject. Thus, the wearable device may be convenient to wear by the subject and need not affect daily life of the subject while the device is worn. The wearable device may ensure that a measured bioimpedance signal of high quality is acquired, which may facilitate long-term monitoring of the subject using the wearable device.

The bioimpedance signal may be used as input for monitoring a condition of the subject and may thus be used in a sleep monitoring or health monitoring application based on the bioimpedance signal. The wearable device may comprise a display for providing information based on the acquired bioimpedance signal to the subject. Alternatively, the wearable device may comprise a communication unit for communicating an acquired signal, which may or may not have been pre-processed in the wearable device, such that an external unit may further process the measured bioimpedance signal and extract information from the signal.

According to a third aspect, there is provided a method for bioimpedance signal acquisition comprising, in an electronic system according to the first aspect: generating a current signal and applying that signal to a subject; measuring a bioimpedance signal based on a voltage generated by the current signal applied to the subject; detecting an AC and/or a DC level of the measured bioimpedance signal and detecting whether the AC and/or DC level of the measured bioimpedance signal is within or outside an AC reference value range and a DC reference value range, respectively; and modifying at least one parameter of the current signal injection module and/or the bioimpedance signal measurement module based on the detected AC and/or a DC level of the measured bioimpedance signal being within or outside an AC reference value range and a DC reference value range, respectively.

Effects and features of this third aspect are largely analogous to those described above in connection with the first and second aspects. Embodiments mentioned in relation to the first and second aspects are largely compatible with the third aspect.

Thus, according to the method, adaptive bioimpedance signal acquisition may be achieved such that high quality data may be acquired even if a subject changes posture or other conditions affecting bioimpedance signal acquisition are altered.

According to a fourth aspect, a tangible, non-transitory computer-readable media has instructions encoded therein that, when executed by one or more processors, cause a system according to the first aspect to perform a method for bioimpedance signal acquisition according to the third aspect.

Effects and features of this fourth aspect are largely analogous to those described above in connection with the first, second, and third aspects. Embodiments mentioned in relation to the first, second, and third aspects are largely compatible with the fourth aspect.

The computer program product may thus control a processing unit to perform the method for bioimpedance signal acquisition such that high quality data may be acquired.

According to a fifth aspect, there is provided an electronic system for bioimpedance signal acquisition for sleep monitoring, comprising: a current signal injection module configured for generating a current signal that is to be applied to a subject; a bioimpedance signal measurement module configured for measuring a bioimpedance signal based on a voltage generated by the current signal applied to the subject; a data quality detection module configured for detecting an AC and a DC level of the measured bioimpedance signal and detecting whether the AC and/or DC level of the measured bioimpedance signal is within or outside an AC reference value range and a DC reference value range, respectively, the data quality detection module being further configured to, upon the AC level being detected to be within or outside the AC reference value range, detect whether the AC level remains within or outside the AC reference value range for a period of time; and a signal adaptation module configured for modifying at least one parameter of the current signal injection module and/or the bioimpedance signal measurement module based on the detection whether the AC and/or DC level of the measured bioimpedance signal is within or outside an AC reference value range and a DC reference value range, respectively and whether the AC level remains within or outside the AC reference value range for a period of time so as to avoid signal adaptation based on a respiratory event.

Effects and features of this fifth aspect are largely analogous to those described above in connection with the first, second, third, and fourth aspects. Embodiments mentioned in relation to the first, second, third, and fourth aspects are largely compatible with the fifth aspect.

According to the fifth aspect, the bioimpedance signal acquisition may be specifically suited for sleep monitoring. The settings of bioimpedance signal acquisition may be altered, which may allow the bioimpedance measurement to continuously be acquired with high data quality. Further, through the data quality detection module detecting both an AC level and a DC level and detecting whether the AC level remains within or outside the AC reference value range for a period of time, the electronic system may be specifically adapted to handle respiratory events, such that the settings of bioimpedance signal acquisition are not triggered when a bioimpedance signal quality deteriorates due to the respiratory event.

The signal adaptation may be immediately triggered if the DC level of the measured bioimpedance signal indicates a saturation or close to saturation of the measured bioimpedance signal, since this may imply that no information may be extracted from the measured bioimpedance signal. However, if the AC level does not correspond to acceptable levels, this may be due to a respiratory event causing the AC level to decrease. Hence, signal adaptation may be withheld until it may be determined that a deteriorated signal quality is not due to a respiratory event.

The electronic system thus allows detecting bioimpedance during respiratory events with a lower data quality which is due to the respiratory event occurring. Hence, the settings of bioimpedance signal acquisition may be triggered only when acquisition conditions require a change.

BRIEF DESCRIPTION OF THE FIGURES

The above, as well as additional, features will be better understood through the following illustrative and non-limiting detailed description of example embodiments, with reference to the appended drawings.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

Figure 1:
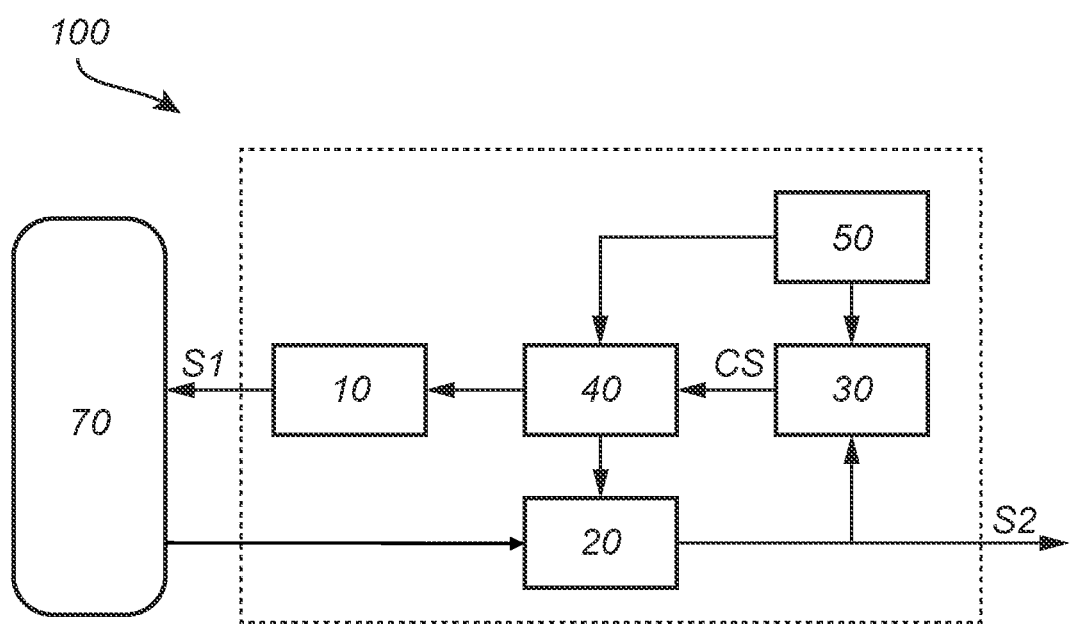
FIG. 1 is a schematic view of a system, according to an example embodiment.

FIG. 1 illustrates an electronic system 100 for bioimpedance signal acquisition. The system 100 is configured to generate a current signal S1 that is to be applied to a subject and to measure a bioimpedance signal S2 providing information of the bioimpedance of the subject, which may be further processed, e.g. for monitoring respiration of the subject. The system 100 is configured to adaptively change settings in order to maintain desired data quality of the measured bioimpedance signal S2.

As shown in FIG. 1, the system 100 comprises a current signal injection module 10. The current signal injection module 10 may be configured to generate and output the current signal S1, which is to be applied to the subject. The current signal injection module 10 may comprise a current source for generating a current signal S1. The current signal injection module 10 may further comprise settings, which may be used for controlling the current signal S1 being generated and output by the current injection module 10.

The current signal injection module 10 may be configured to output an AC current signal. The settings of the current signal injection module 10 may control an amplitude and a frequency of the generated current signal S1.

The system 100 further comprises a bioimpedance signal measurement module 20. The bioimpedance signal measurement module 20 may be configured to receive voltage input signals representing a voltage generated by the current signal S1 applied to the subject. The bioimpedance signal measurement module 20 may be configured to extract a measured bioimpedance signal S2 from the received voltage input signals.

The bioimpedance signal measurement module 20 may comprise settings, which may be used for controlling the extraction of the bioimpedance signal S2 from the received voltage input signals. For instance, a gain of the measured bioimpedance signal S2 may be controlled by the settings.

The bioimpedance signal measurement module 20 may be configured to process the received voltage input signals, e.g. by filtering the input signals, in order to extract relevant information. The filtering of the input signals may also be controlled by settings of the bioimpedance signal measurement module 20 or may be performed according to a fixed set-up.

The bioimpedance signal measurement module 20 may output the measured bioimpedance signal S2, which may be used for determining a condition of the subject by further processing of the measured bioimpedance signal S2. For instance, the measured bioimpedance signal S2 may be used for monitoring respiration of the subject. The further processing of the measured bioimpedance signal S2 may be performed by an analysis module within the system 100. However, according to an alternative, the measured bioimpedance signal S2 is output to an external unit for further processing.

The system 100 further comprises a data quality detection module 30, which is configured to receive the measured bioimpedance signal S2. The data quality detection module 30 may be configured to detect and AC level and/or a DC level of the measured bioimpedance signal S2.

The data quality detection module 30 may further store an AC reference value range and/or a DC reference value range. The AC reference value range and/or the DC reference value range may be set to define acceptable AC levels and DC levels, respectively, for high quality data acquisition. Alternatively, the AC reference value range and/or the DC reference value range may be set to define non-acceptable AC levels and DC levels, respectively, for high quality acquisition.

The data quality detection module 30 may be configured to detect whether the AC level and/or the DC level of the measured bioimpedance signal S2 is within or outside the AC reference value range and the DC reference value range, respectively. For instance, the data quality detection module 30 may compare the detected AC level and/or the detected DC level to the AC reference value range and the DC reference value range, respectively.

In this way, the data quality detection module 30 may be configured to determine whether data quality is not within acceptable limits, based on the relation of the AC level and/or the DC level to the AC reference value range and the DC reference value range, respectively.

When the data quality detection module 30 detects that the measured bioimpedance signal S2 is of a non-acceptable data quality, a control signal CS may be output by the data quality detection module 30.

The system 100 further comprises a signal adaptation module 40, which is configured for modifying at least one parameter of the current signal injection module 10 and/or the bioimpedance signal measurement module 20. The signal adaptation module 40 may thus be configured to cause a change settings of the system 100 so as to adaptively change the system 100. The changing of the settings may ensure that a high quality bioimpedance signal S2 is acquired even if conditions in which the bioimpedance signal S2 is acquired are changed.

The signal adaptation module 40 may be configured for modifying at least one parameter of the current signal injection module 10 and/or the bioimpedance signal measurement module 20 based on whether the AC level and/or the DC level of the measured bioimpedance signal S2 is within or outside the AC reference value range and the DC reference value range, respectively. This implies that the AC level and/or the DC level of the measured bioimpedance signal S2 may be used as quality measure(s) of the bioimpedance signal acquisition and the signal adaptation module 40 may be configured to perform parameter modification based on the quality measure(s).

The signal adaptation module 40 may be configured to send parameter modification signals to the current signal injection module 10 and/or the bioimpedance signal measurement module 20. The parameter modification signal may comprise information that a parameter is to be modified and may comprise a new value of the parameter. Alternatively, the parameter modification signal may indicate whether a value of the parameter is to be increased or decreased.

The signal adaptation module 40 may be configured to modify at least one of an amplitude of the generated current signal S1, a frequency of the generated current signal S1, and a gain of the measured bioimpedance signal S2.

The system 100 may further comprise electrodes 70, which may be integrated with the system 100 and may be connected to the current signal injection module 10 and the bioimpedance signal measurement module 20. Alternatively, the electrodes 70 may be configured to be connected to the system 100.

The electrodes 70 may be configured to be attached to the subject for applying the current signal S1 to the subject and for detecting a voltage generated by the current S1 passing through tissue of the subject. Two or more electrodes 70 may be used and the electrodes 70 may be configured for injecting the current signal S1 and detecting a voltage by the same or by different electrodes 70. Having more than two electrodes 70 may also allow selectively choosing which electrodes 70 that should be part of the pair(s) used for injecting the current signal S1 and detecting the voltage generated by the current signal S1.

The signal adaptation module 40 may further be configured to select which electrodes 70 that are to be included in the electrode pair for measuring the bioimpedance signal. The signal adaptation module 40 may in this regard send a parameter modification signal to the bioimpedance signal measurement module 20 for controlling which input signals that are to be selected by the bioimpedance signal measurement module 20.

During a process of parameter modification, the signal adaptation module 40 may send parameter modification signals to the current signal injection module 10 and/or the bioimpedance signal measurement module 20. Then, a quality of the measured bioimpedance signal S2 based on changed parameters, may be detected in the data quality detection module 30. As long as the quality is not acceptable, the at least one parameter may be continuously modified by further parameter modification signals from the signal adaptation module 40. When an acceptable data quality is detected by the data quality detection module 30, a new control signal CS may be sent to the signal adaptation module 40 terminating the process of parameter modification.

The AC reference value range and the DC reference value range may also be changed in association with parameter modification. For instance, if the parameter modification process results in that a best possible signal quality is not within desired ranges, the AC reference value range and the DC reference value range may be changed such that the data quality detection module will not constantly trigger a parameter modification. This may allow acquiring bioimpedance signal of a relatively high quality. When it is detected that a higher quality signal may again be acquired, the AC reference value range and the DC reference value range may again be changed for controlling the system to acquire signal quality within desired ranges.

The data quality detection module 30 may be configured to continuously detect quality of the measured bioimpedance signal S2. Thus, as soon as signal quality deteriorates, this may be detected in the data quality detection module 30.

Alternatively, the data quality detection module 30 may be configured to detect quality at predetermined intervals. This may be regular intervals or intervals depending on input that may indicate a likelihood of data quality deteriorating. By the data quality detection module 30 detecting quality at intervals, data processing power may be saved, while allowing detection of unacceptable data quality fairly quickly. For instance, the data quality detection module 30 may detect quality every 10 seconds.

Adaptation of the system 100 for bioimpedance signal acquisition may be needed when the subject changes posture. The posture change may for instance affect a relation between electrodes 70 and/or between electrodes 70 and the subject. Thus, a posture change may often be associated with a need of adapting the system 100.

The system 100 may further comprise a posture detection module 50. The posture detection module 50 may be configured to receive information relevant to a subject's posture from a sensor, such as an accelerometer mounted on the subject and/or a camera monitoring a scene in which the subject is located. The posture detection module 50 may be configured to process the information in order to determine a posture of the subject.

The posture detection module 50 need not necessarily determine an absolute posture of the subject. According to an alternative, the posture detection module 50 may be configured to determine that a posture change occurs.

When the posture detection module 50 determines a changed posture (or a change in posture), the posture detection module 50 may provide a signal to the signal adaptation module 40 in order to trigger parameter modification. Alternatively or additionally, the posture detection module 50 may provide a signal to the data quality detection module 30 in order to trigger checking of quality of the measured bioimpedance signal S2, which may in turn trigger parameter modification.

The system 100 may be calibrated to adapt the system 100 to a subject. Thus, the system 100 may be personalized and parameters for acquiring bioimpedance signals of high quality for the subject may be determined. The parameters may differ substantially between different subjects, e.g. since bioimpedance may vary between different subjects. Also, the parameters may differ depending on placement of electrodes on the subject, so calibration may be needed before each session of bioimpedance signal acquisition, even for the same subject.

Results of the calibration may be stored in a memory within the system 100. Thus, parameters may be retrieved from the memory. The calibration may be performed based on different postures, such that when a change to a specific posture is detected by the posture detection module 50, parameters for the specific posture may be retrieved from the memory. Thus, the system 100 may immediately be set to use parameters, which should enable the system 100 to acquire the measured bioimpedance signal S2 with a high quality for the changed posture. This may imply setting the at least one of the amplitude of the current signal S1, the frequency of the signal S1, the gain of the measured bioimpedance signal S2 and the electrodes to be included in the electrode pair for measuring the bioimpedance signal. Also, setting the parameters may include setting the AC reference value range and the DC reference value range to be used by the data quality detection module 30.

As described in more detail below, the calibration need not beforehand determine settings for different postures. The settings may alternatively be determined when a posture is first detected and, then, the settings for the posture may be stored in order to enable re-use.

The data quality detection module 30 may be configured to detect whether the change to parameters does provide an output of a high quality measured bioimpedance signal S2. If not, further parameter modification may be triggered.

The system 100 may comprise a memory, which may store the calibration data. The memory may be accessible for each of the current signal injection module 10, the bioimpedance signal measurement module 20, the data quality detection module 30 in order to retrieve settings for the modules. Alternatively or additionally, the memory may be accessible by the signal adaptation module 40, which may then send information of the settings to the other modules. The system 100 may comprise a single memory which is accessible by the modules. Alternatively, each module may comprise an internal memory which stores calibration data relevant for that module.

Each of the modules 10, 20, 30, 40, 50 may be implemented in hardware, or as any combination of software and hardware. At least part of the modules 10, 20, 30, 40, 50 may, for instance, be implemented as software being executed on a general-purpose computer. The system 100 may thus comprise one or more processing units, such as a central processing unit (CPU), which may execute the instructions of one or more computer programs in order to implement functionality of the modules. Thus, the system 100 may comprise a single processing unit, which may provide functionality of each of the modules 10, 20, 30, 40, 50, e.g. as separate threads within the processing unit.

The modules 10, 20, 30, 40, 50 may alternatively be implemented as firmware arranged e.g. in an embedded system, or as a specifically designed processing unit, such as an Application-Specific Integrated Circuit (ASIC) or a Field-Programmable Gate Array (FPGA).

The current signal injection module 10 may comprise circuitry for converting control instructions, which may be implemented in software and/or hardware, to an actual current signal S1, which may be output to electrodes 70 for being applied to a subject.

The bioimpedance signal measurement module 20 may comprise circuitry for converting control instructions, which may be implemented in software and/or hardware, to form a bioimpedance signal based on received input voltage signals.

The system 100 may comprise a housing, in which the modules 10, 20, 30, 40, 50 may be arranged. The system 100 may thus be delivered in a single package and may comprise an interface for putting the system 100 into use.

The housing may for instance comprise ports, to which electrodes 70 may be connected for receiving the current signal S1 and providing voltage signals representing a bioimpedance. Alternatively, electrodes 70 may be pre-attached to the housing on delivery of the system 100.

The housing may further comprise an output port for connection to an external unit, which may receive the measured bioimpedance signal S2 for further processing of the signal. Alternatively or additionally, the housing may comprise a communication unit for wireless communication of the bioimpedance signal S2 to the external unit.

The housing may further comprise additional ports for connecting further units to the system 100, such as one or more sensors for detecting posture of the subject.

The housing may be configured to be worn by a subject, such that the system 100 allowing acquisition of the measured bioimpedance signal S2 with high quality may be worn and used for long-term monitoring of the subject. The housing may comprise a strap for attaching the housing to or around a body part of the subject or may have a shape so as to allow the housing to be worn by the subject.

Referring now to FIGS. 2-8, use of the system 100 in bioimpedance signal acquisition will be further described.

Figure 2:
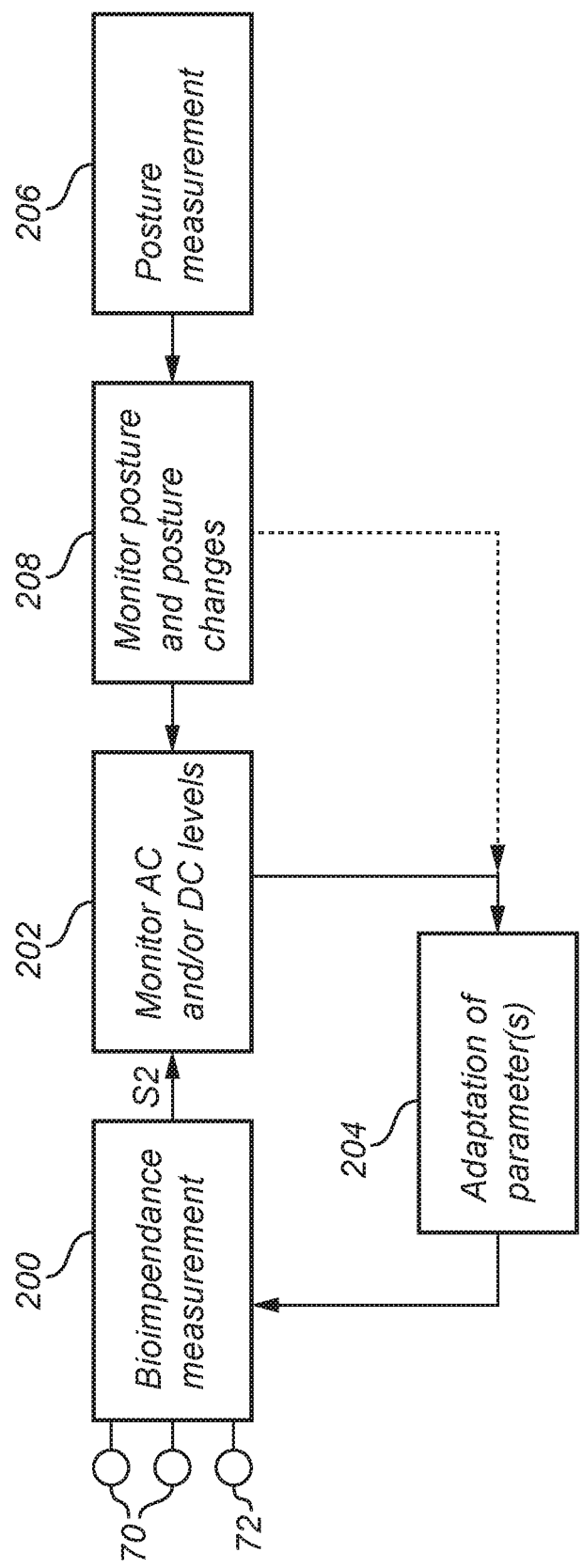
FIG. 2 is a schematic view of a method for bioimpedance signal acquisition, according to an example embodiment.

FIG. 2 illustrates a general overview of bioimpedance signal acquisition. As shown in FIG. 2, two or more electrodes 70 may be attached to a subject. A further electrode 72, which may provide a bias voltage may optionally be used.

The system 100 measures 200 a bioimpedance signal using a set amplitude and frequency of a current signal S1, set gain of the bioimpedance signal measurement module 20 and set electrode pair as input to the bioimpedance signal measurement module 20.

The measured bioimpedance signal S2 may be provided as a digital or analog signal. The AC level and/or DC level may be monitored 202 by the data quality detection module 30. If it is determined that the AC level and/or DC level is within or outside the AC reference value range and the DC reference value range, respectively, adaptation 204 of the parameters for bioimpedance signal acquisition may be performed. Then, the system 100 may again measure 200 the bioimpedance signal using the new parameter(s).

As also illustrated in FIG. 2, a sensor, e.g. an accelerometer, may acquire 206 a signal representing posture of the subject. The acquired signal may be monitored 208 in order to determine an absolute posture and/or determine a change in posture. If the posture monitoring reveals that a posture has changed, a signal may be sent for triggering the monitoring 202 of the AC level and/or the DC level of the measured bioimpedance signal S2.

Optionally, if posture dependent settings have been stored, a signal may also be sent for triggering adaptation 204 of the parameters for bioimpedance signal acquisition (using stored parameter settings).

Figure 3:
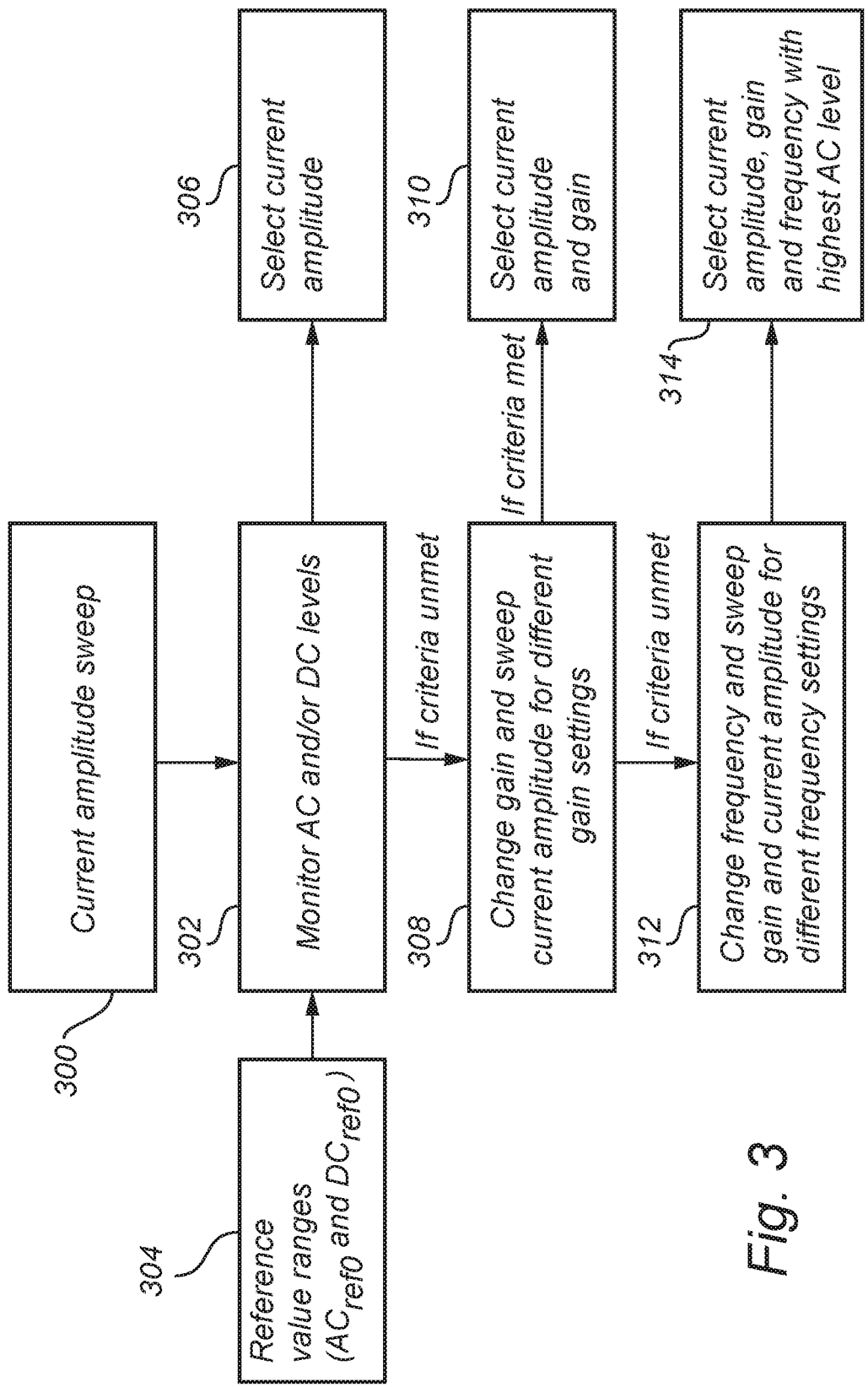
FIG. 3 is a schematic view of a method of calibration of a system, according to an example embodiment.

Referring now to FIG. 3, a calibration procedure will be described. The calibration may be performed before each session of bioimpedance signal acquisition. The calibration may determine settings for a subject and for a placement of the electrodes 70 on the subject. Calibration data may be stored by the system 100 for re-use between different sessions on a subject, such that calibration need not necessarily be performed before each session.

The calibration may be performed for several different postures, such that calibration data applying to each posture may be stored. This may allow retrieving settings based on detection of a specific posture.

According to an alternative, the calibration is only performed for one posture in order to initialize bioimpedance measurements. This may allow quickly starting bioimpedance measurements, but the system 100 may not as quickly adapt to new postures.

According to an embodiment, illustrated in FIG. 3, the calibration may start by providing settings of the frequency of the current signal S1 and the gain of the measured bioimpedance signal S2 to generate as large signal as possible. An amplitude of the current signal S1 is swept 300 over all possible current amplitudes.

During sweeping of the amplitude of the current signal S1, the measured bioimpedance signal S2 is acquired for each setting of the amplitude. The AC level and/or DC level of the measured bioimpedance signal S2 is monitored 302. The AC reference value range and/or the DC reference value range may be provided 304 as input to the monitoring of the AC and/or DC levels. The AC reference value range and/or the DC reference value range may be set as fixed values in the system 100 or may be based on subject characteristics, which may be manually input. The subject characteristics may include body mass index (BMI) of the subject, gender of the subject, and position of electrodes 70 on the subject.

The monitoring of the AC level and/or DC level may compare the AC and/or DC levels to the AC reference value range and the DC reference value range, respectively, in order to determine whether the AC level and/or DC level are within acceptable ranges as set by the AC reference value range and/or the DC reference value range.

The AC reference value range may indicate whether respiration information may be extracted from the measured bioimpedance signal. The AC reference value range may according to an embodiment be set as exceeding 90% of a reference value, $AC_{ref0}$. The reference value may be based on a desired signal-to-noise ratio (SNR) and may be based on a fixed pre-set value or a value dependent on subject characteristics as mentioned above. The reference value may be related to a level of the detected signal so that, if the AC level is at least 90% of the reference value, the SNR will be acceptable. However, it should be realized that the AC reference value may be set to any value and then, the AC reference value range may be correspondingly set based on a percentage of the AC reference value depending on which AC reference value is chosen. Hence, the AC reference value range may correspond to at least 80% of the reference value or 100% of the reference value, instead.

In one embodiment, the AC reference value may initially be set to a default value that is known to give reliable measurement results. Then, the AC reference value may be updated to correspond to an AC level providing highest signal quality during the calibration process which will be further described below.

The DC reference value range may indicate whether saturation of the signal occurs. Thus, the DC reference value range may in one embodiment be defined as 5-95% of an operation range $DC_{ref0}$ of the system 100. Thus, by the DC level being within the DC reference value range, the measured bioimpedance signal S2 will not be saturated and information may be extracted from the signal.

The AC reference value range and the DC reference value range may be defined in relation to a respective reference value. Thus, a single reference value may be provided, such that, when monitoring the AC and/or DC levels, the AC reference value range and the DC reference value range may be formed based on input of a single value.

The AC level may be measured as a voltage difference between a peak representing a maximum value and a following peak representing a minimum value. The DC level may be measured as an average voltage around which the AC level oscillates.

If the criterion or criteria are met, the calibration may be terminated and a setting of the amplitude of the current signal S1 may be selected 306. The settings of the frequency of the current signal S1 and the gain of the measured bioimpedance signal S2 generating best signal quality are also selected.

If only the DC level is monitored, the current amplitude generating a highest DC level signal without exceeding a saturation criterion set by the DC reference value range may be selected.

If only the AC level is monitored, the current amplitude generating a highest AC level may be selected.

If both the AC level and the DC level are monitored, the current amplitude generating a DC level signal within the DC reference value range and a highest AC level may be selected.

If the criterion or criteria are not met by any of the amplitude settings of the injected current signal S1, a gain of the bioimpedance signal measurement module 20 is changed to the next level and a new current amplitude sweep is made. This is repeated 308 for different gain settings, changing the gain in steps from a gain providing a highest signal level to a gain providing a lowest signal level of the measured bioimpedance signal S2. During the changing of gain level and current amplitude sweep, the AC and/or DC levels are monitored, as explained above in step 304.

Again, if the criterion or criteria are met, the calibration may be terminated and settings of the parameters may be selected 310. The settings of the frequency of the current signal S1 generating best signal quality may then be selected together with a gain and a current amplitude based on the sweep. If the criterion or criteria are met, the gain need not be changed to check all possible gains, but rather the gain level for which the criterion or criteria are met may be selected. Further, the current amplitude may be selected based on highest AC or DC level as described above.

If the criterion or criteria are still not met by any of the combination of amplitude settings of the injected current signal S1 and the gain of the bioimpedance signal measurement module 20, a frequency of the current signal S1 is changed to the next level. Then, a new sweep of the gain of the bioimpedance signal measurement module 20 and the amplitude of the injected current signal S1 as made in step 308 is repeated. This is repeated 312 for different frequency settings, changing the frequency in steps from a frequency providing a highest signal level to a frequency providing a lowest signal level of the measured bioimpedance signal S2. During the changing of the frequency level, the gain level and the current amplitude sweep, the AC and/or DC levels are monitored, as explained above in step 304.

Again, if the criterion or criteria are met, the calibration may be terminated and settings of the parameters may be selected 314. The settings of the amplitude and frequency of the current signal S1, and the gain may then be selected based on highest AC or DC level as described above. All levels of frequencies need not be swept, but rather the frequency level for which the criterion or criteria are met may be selected.

It should also be realized that an order in which parameters are changed during calibration need not necessarily be in the order described above. Rather, parameters may be changed in any order for determining settings.

In an embodiment, the amplitude of the current signal S1 may be varied between 10 µA and 1 mA using a step size of 10 µA. The gain of the bioimpedance signal measurement module 20 may be varied between 50 V/V and 500 V/V using a step size of 10 V/V. The frequency of the current signal S1 may be varied between 1 kHz and 1 MHz using a step size of 10 kHz. It should be realized that other ranges and step sizes may be used.

Figure 4:
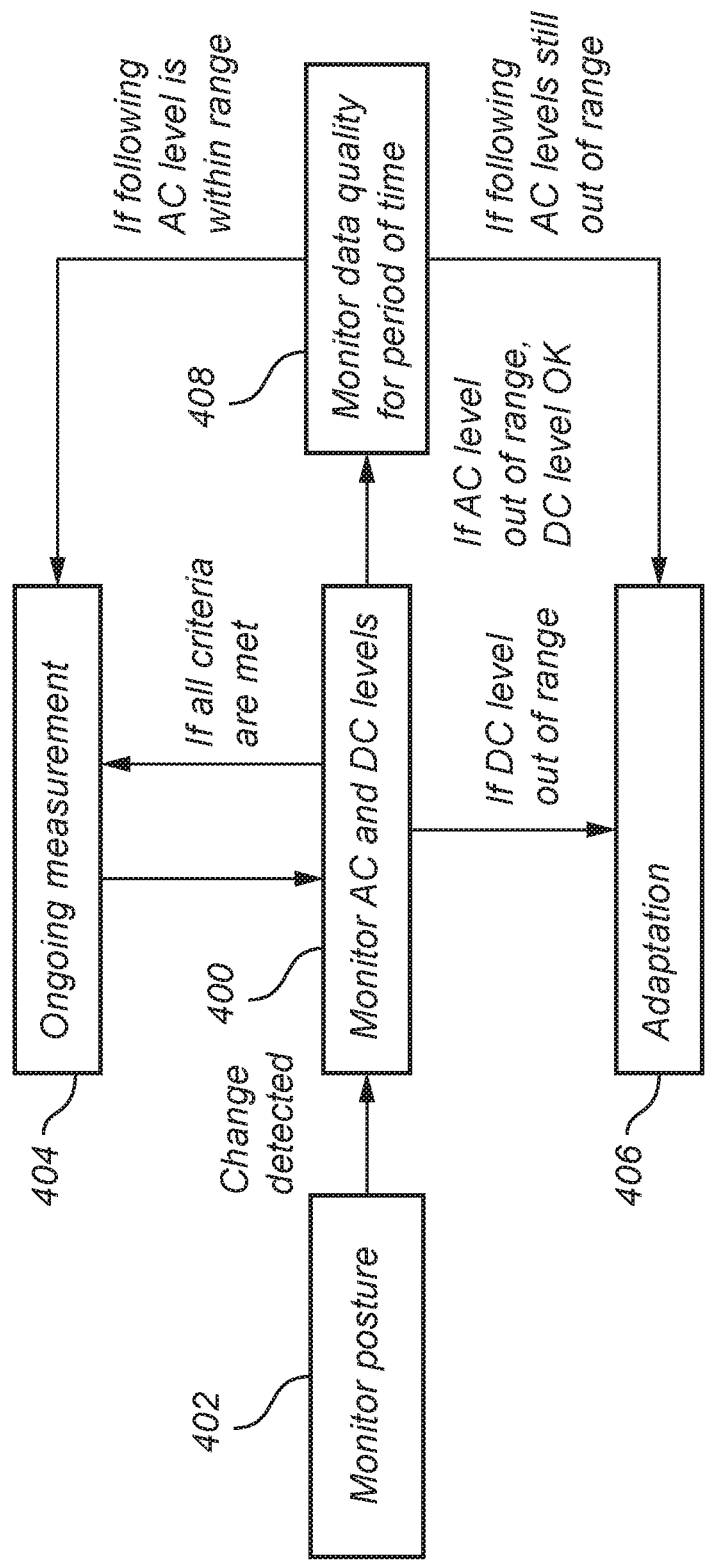
FIG. 4 is a schematic view of a method of bioimpedance signal acquisition taking respiratory events into account, according to an example embodiment.

Referring now to FIG. 4, data quality monitoring in relation to both the AC and the DC level of the measured bioimpedance signal will be described. Thus, the adaptive bioimpedance signal acquisition is in this embodiment based on both AC and DC level of the signal. This adaptive bioimpedance signal acquisition may be especially suitable for sleep monitoring or in any other situation where respiratory events may be expected, as the adaptation is configured to take into account that loss of data quality may be due to respiratory events.

The AC and DC levels are monitored 400. The AC and DC levels may be extracted from the measured bioimpedance signal S2 at regular time intervals. For instance, the AC and DC levels may be extracted every 10 seconds, which allows quickly detecting a low data quality, without requiring constantly determining the AC and DC levels.

The AC and DC levels may be extracted based on input of a posture change from posture monitoring 402, if such is performed. The detection of a posture change may indicate a likelihood that the bioimpedance signal acquisition may need adaptation and, therefore, may trigger extra monitoring of AC and DC levels.

The AC and DC levels may be monitored and compared to AC reference value range and DC reference value range as set during calibration. It should be noted that at least the AC reference value range may be set in dependence on the chosen settings during calibration.

If both the AC level and the DC level are within the AC reference value range and the DC reference value range, i.e. indicate that the data quality is acceptable, measurement of the bioimpedance may be ongoing 404 and no signal adaptation is necessary.

If the DC level is out of range, the measured bioimpedance signal S2 is saturated, which implies that information may not be extracted. Thus, if it is detected that the DC level is out of range, adaptation 406, as will be described later, may be initiated.

If the AC level is out of range, i.e. the AC signal level is low, this may be due to a respiratory event, such as apnea, shallow breathing or hypopnea. Thus, adaptation of the bioimpedance signal acquisition may not necessarily be needed or should not even be performed, as adaptation should be performed based on conditions of acquiring the bioimpedance signal changing, not based on the bioimpedance information changing.

Hence, if it is detected that the AC level is out of range, but the DC level is still within the range of the DC reference value range, data quality may be continuously monitored 408 for a period of time. For instance, the data quality may be monitored for 60 seconds. Thus, data quality may be monitored during such a long period of time that, if the AC level being out of range was due to a respiratory event, normal respiration may be resumed.

The DC level may also be used in order to determine whether a detection of the AC level being out of range relates to a change that needs signal adaptation (such as due to a change in posture) or relates to a respiratory event. If the AC level is detected to be out of range and it is simultaneously detected that the DC level has changed, the change may likely be due to a posture change and not due to a respiratory event. Then, adaptation 406 may be initiated. However, if the DC level has not changed, the detection of the AC level being out of range has a higher likelihood to be due to a respiratory event and data quality may then be continuously monitored 408 for a period of time.

If the AC level returns to being within the AC reference value range, ongoing measurement 404 of the bioimpedance signal may be resumed and no signal adaptation is necessary.

If, on the other hand, the AC level does stay outside the AC reference value range, it may be determined that the change in AC level was not due to a respiratory event. Hence, adaptation 406, as will be described later, may be initiated.

As an alternative or in addition to monitoring the AC level and the DC level for a period of time, the system 100 may comprise additional sensor(s) which may be configured to detect respiratory events. Such sensor(s) may e.g. measure whether any chest movement occurs for detecting apnea. Also, the bioimpedance measurement may be used for detecting respiratory events. Thus, if a respiratory event is detected, the ongoing measurement 406 may continue and the monitoring 400 of the AC and DC levels may be performed again at regular time intervals.

Figure 5:
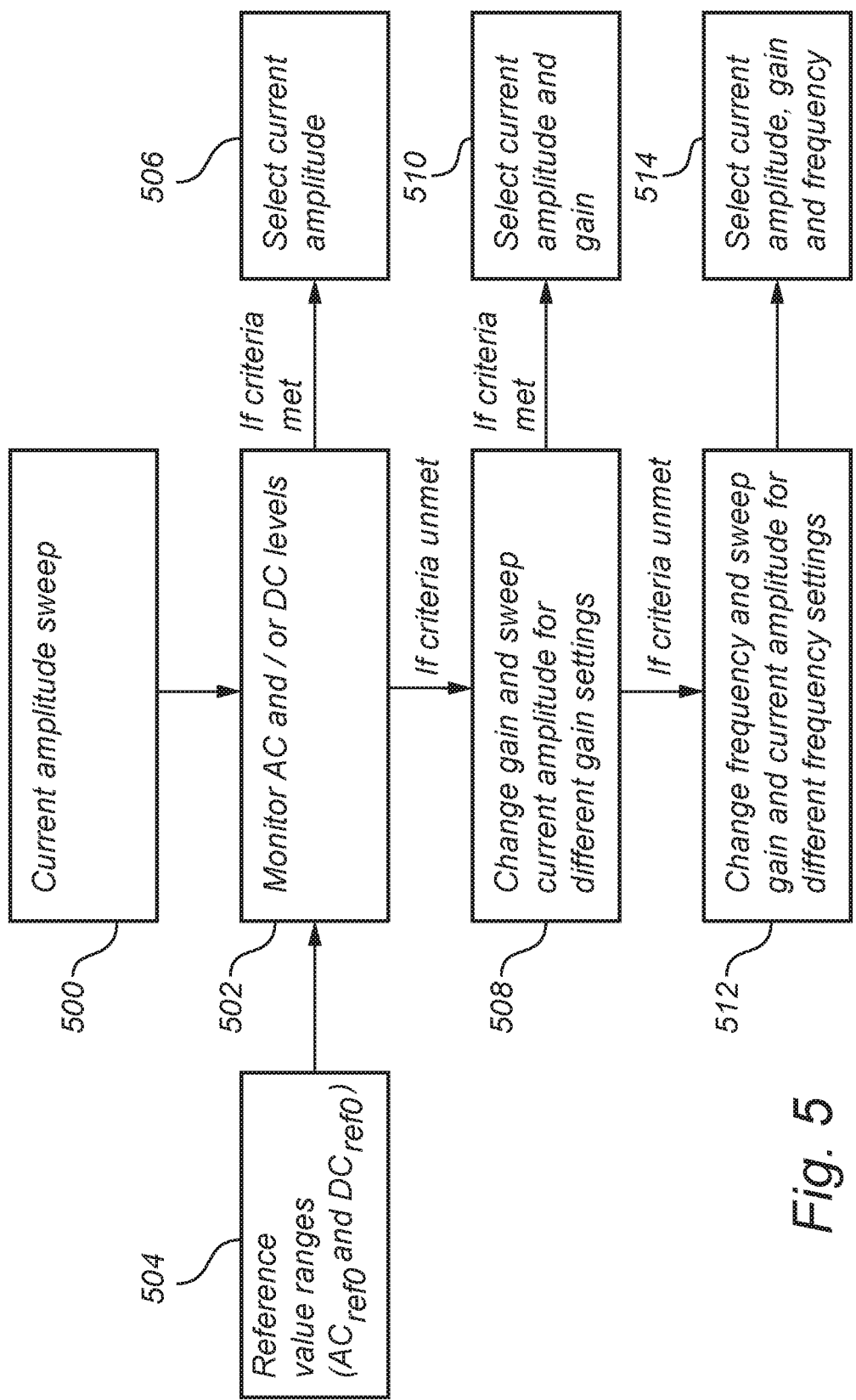
FIG. 5 is a schematic view of a method of adapting bioimpedance signal acquisition, according to an example embodiment.

Referring now to FIG. 5, parameter modification according to a first embodiment of adaptation of the bioimpedance signal acquisition will be described. The parameter modification according to the first embodiment resembles the calibration process as described above with reference to FIG. 3.

The adaptation according to the first embodiment aims to establish settings that provide a high quality bioimpedance signal. The settings are established without any prejudice to certain settings previously used.

Thus, similar to the calibration described with reference to FIG. 3, the adaptation may start by providing settings of the frequency of the current signal S1 and the gain of the measured bioimpedance signal S2 to generate best signal quality. An amplitude of the current signal S1 is swept 500 over all possible current amplitudes.

During sweeping of the amplitude of the current signal S1, the measured bioimpedance signal S2 is acquired for each setting of the amplitude. The AC level and/or DC level of the measured bioimpedance signal S2 is monitored 502. The AC reference value range and/or the DC reference value range may be provided 504 as input to the monitoring of the AC and/or DC levels, or a single value may be provided as input allowing forming of the AC reference value range and the DC reference value range. At least the AC reference value range may be based on an adapted AC reference value $AC_{ref}$, which may be set during use of the system 100 and does not necessarily correspond to the AC reference value $AC_{ref0}$ as used during calibration. The DC reference value range may be based on the same DC reference value $DC_{ref0}$ as used during calibration.

The monitoring of the AC level and/or DC level may compare the AC and/or DC levels to the AC reference value range and the DC reference value range, respectively, in order to determine whether the AC level and/or DC level are within acceptable ranges as set by the AC reference value range and/or the DC reference value range.

As explained for calibration above, if the criterion or criteria are met, the adaptation may be terminated and a setting of the amplitude of the current signal S1 may be selected 506. The settings of the frequency of the current signal S1 and the gain of the measured bioimpedance signal S2 generating best signal quality are also selected.

Further, as explained for calibration above, if the criterion or criteria are not met by any of the amplitude settings of the injected current signal S1, the gain of the bioimpedance signal measurement module 20 is changed 508 and current amplitude sweeps are made for different gain settings, while monitoring the AC and/or DC levels.

Again, if the criterion or criteria are met, the calibration may be terminated and settings of the parameters may be selected 510 based on highest AC or DC level of the signal.

If the criterion or criteria are still not met by any of the combination of amplitude settings of the injected current signal S1 and the gain of the bioimpedance signal measurement module 20, a frequency of the current signal S1 is changed to the next level. Then, a new sweep of the gain of the bioimpedance signal measurement module 20 and the amplitude of the injected current signal S1 as made in 508 is repeated. This is repeated 512 for different frequency settings, while the AC and/or DC levels are monitored.

Again, if the criterion or criteria are met, the adaptation may be terminated and settings of the parameters may be selected 514. The settings of the amplitude and frequency of the current signal S1, and the gain may then be selected based on highest AC level of the signal.

If the criteria are still not met, it may be determined that the criteria may not be met and the settings providing best results may be used. Thus, the adaptation may end with the setting of the amplitude, the gain and the frequency being updated with values for which best results are obtained.

Figure 6:
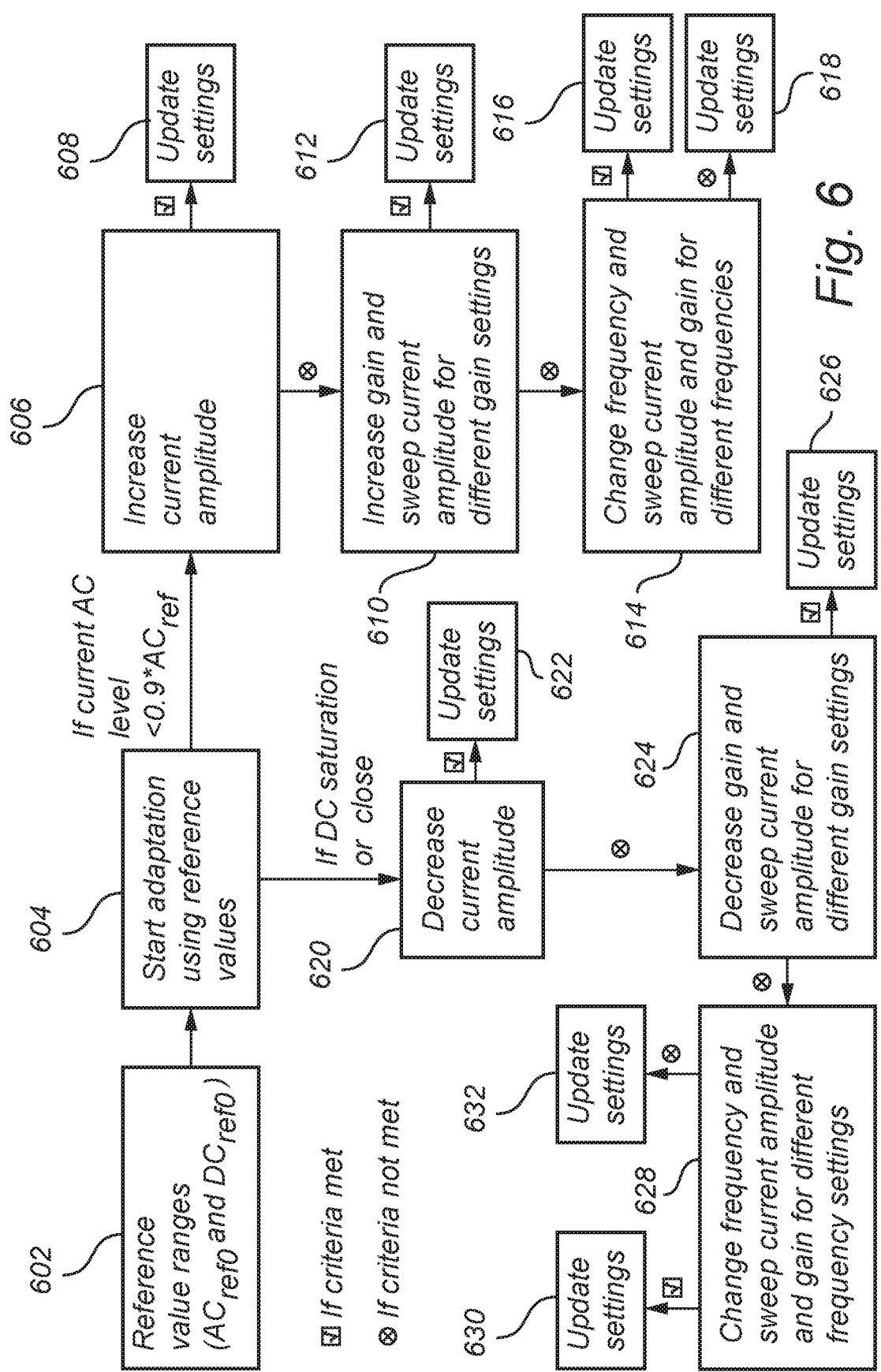
FIG. 6 is a schematic view of a method of adapting bioimpedance signal acquisition, according to an example embodiment.

Referring now to FIG. 6, parameter modification according to a second embodiment of adaptation of the bioimpedance signal acquisition will be described. The parameter modification according to the second embodiment makes use of previous settings and tries to change the settings based on the previous settings in order to quickly arrive at an adapted bioimpedance signal acquisition which provides high quality data.

The adaptation receives 602 the AC reference value range and/or the DC reference value range as input to the monitoring of the AC and/or DC levels, or a single value may be received as input allowing forming of the AC reference value range and the DC reference value range. At least the AC reference value range may be based on an adapted AC reference value $AC_{ref}$, which may be set during use of the system 100 and does not necessarily correspond to the AC reference value $AC_{ref0}$ as used during calibration. The DC reference value range may be based on the same DC reference value $DC_{ref0}$ as used during calibration.

The adaptation is started 604 monitoring the AC level and/or the DC level against the AC reference value range $AC_{ref}$ and the DC reference value range $DC_{ref0}$. Also, the current parameter values of the at least one parameter of the current signal injection module 10 and the bioimpedance signal measurement module 20 are used as initial values.

If it is found that the AC level is outside the AC reference value range, e.g. $<0.9*AC_{ref}$, it may be determined that an increase in the amplitude of the measured bioimpedance signal S2 is needed. Thus, the adaptation may use the present settings of parameter values and adapt the bioimpedance signal acquisition in relation to the present settings.

First, values of the gain of the bioimpedance signal measurement module 20 and the frequency of the current signal S1 according to the present settings may be maintained. The amplitude of the current signal S1 may be increased 606 in sequential steps. During increasing of the amplitude of the current signal S1, the measured bioimpedance signal S2 is acquired for each setting of the amplitude. The AC level and the DC level of the measured bioimpedance signal S2 is monitored and compared to the AC reference value range and the DC reference value range, respectively. Thus, it is determined whether the criteria are met and the increasing of the amplitude of the current signal S1 is continued until the criteria are met or a maximum amplitude is reached.

If the criteria are met, the adaptation may be terminated and the setting of the amplitude is updated 608 with a value for which the criteria are met. Also, the AC reference value $AC_{ref}$ is updated based on the new setting of the amplitude of the current signal S1.

If the criteria are not met by any of the amplitude settings of the injected current signal S1, the gain of the bioimpedance signal measurement module 20 is increased to the next level and a current amplitude sweep is made. This is repeated 610 for different gain settings, changing the gain in steps towards a maximum gain. During the increasing of the gain level and the current amplitude sweep, the AC and DC levels are monitored.

If the criteria are met, the adaptation may be terminated and the setting of the amplitude and the gain are updated 612 with values for which the criteria are met. Also, the AC reference value $AC_{ref}$ is updated based on the new setting of the amplitude of the current signal S1.

If the criteria are not met by any of the combinations of amplitude and gain settings, the frequency of the current signal S1 is changed. Depending on a position on the semi-circular relation in the Cole-Cole plot of the resistance and reactance parts of the measured bioimpedance signal S2, the frequency may be decreased or increased to the next level and a sweep of current amplitude and gain settings is made. This is repeated 614 for different frequency settings, changing the frequency in steps towards a minimum or maximum frequency. During the decreasing or increasing of the frequency level and the gain and current amplitude sweep, the AC and DC levels are monitored.

If the criteria are met, the adaptation may be terminated and the setting of the amplitude, the gain and the frequency are updated 616 with values for which the criteria are met. Also, the AC reference value $AC_{ref}$ is updated based on the new setting of the amplitude of the current signal S1.

If the criteria are not met for any frequency, it may be determined that the criteria may not be met and the settings providing best results may be used. Thus, the adaptation may end with the setting of the amplitude, the gain and the frequency being updated 618 with values for which best results are obtained. Also, the AC reference value $AC_{ref}$ is updated based on the new setting of the amplitude of the current signal S1.

The process of adapting bioimpedance signal acquisition for increasing the AC level may also be performed in relation to a maximum time. Thus, a maximum time may be set, such that parameter modification may not continue for a time period exceeding the maximum time. This implies that a time period during which bioimpedance signal data may not be analyzed is limited, as the bioimpedance signal during parameter modification may not be used as providing reliable data (e.g. because the conditions during which the bioimpedance signal is measured is constantly changed).

Thus, if the adaptation process has not terminated within the maximum time, the settings providing best results may be used. Thus, the adaptation may end when reaching the maximum time with the setting of the amplitude, the gain and the frequency being updated with values for which best results are obtained. Also, the AC reference value $AC_{ref}$ is updated based on the new setting of the amplitude of the current signal S1.

According to an embodiment, the maximum time may be set to at least 30 seconds, which may give reasonable time for allowing adaptation to be performed.

If it is found when the adaptation is started at 604 that the DC level is outside the DC reference value range, e.g. that DC saturation occurs or is close to occurring due to the DC level $>0.95*DC_{ref0}$, it may be determined that a decrease in the amplitude of the measured bioimpedance signal S2 is needed. Thus, the adaptation may use the present settings of parameter values and adapt the bioimpedance signal acquisition in relation to the present settings.

First, values of the gain of the bioimpedance signal measurement module 20 and the frequency of the current signal S1 according to the present settings may be maintained. The amplitude of the current signal S1 may be decreased 620 in sequential steps. During decreasing of the amplitude of the current signal S1, the measured bioimpedance signal S2 is acquired for each setting of the amplitude. The AC level and the DC level of the measured bioimpedance signal S2 is monitored and compared to the AC reference value range and the DC reference value range, respectively. Thus, it is determined whether the criteria are met and the increasing of the amplitude of the current signal S1 is continued until the criteria are met or a minimum amplitude is reached.

If the criteria are met, the adaptation may be terminated and the setting of the amplitude is updated 622 with a value for which the criteria are met. Also, the AC reference value $AC_{ref}$ is updated based on the new setting of the amplitude of the current signal S1.

If the criteria are not met by any of the amplitude settings of the injected current signal S1, the gain of the bioimpedance signal measurement module 20 is decreased to the next level and a current amplitude sweep is made. This is repeated 624 for different gain settings, changing the gain in steps towards a minimum gain. During the decreasing of the gain level and the current amplitude sweep, the AC and DC levels are monitored.

If the criteria are met, the adaptation may be terminated and the setting of the amplitude and the gain are updated 626 with values for which the criteria are met. Also, the AC reference value $AC_{ref}$ is updated based on the new setting of the amplitude of the current signal S1.

If the criteria are not met by any of the combinations of amplitude and gain settings, the frequency of the current signal S1 is changed. Depending on a position on the semi-circular relation in the Cole-Cole plot of the resistance and reactance parts of the measured bioimpedance signal S2 and the frequency of the current signal S1, the frequency may be increased or decreased to the next level and a sweep of current amplitude and gain settings is made. This is repeated 628 for different frequency settings, changing the frequency in steps towards a maximum or minimum frequency. During the increasing or decreasing of the frequency level and the gain and current amplitude sweep, the AC and DC levels are monitored.

If the criteria are met, the adaptation may be terminated and the setting of the amplitude, the gain and the frequency are updated 630 with values for which the criteria are met. Also, the AC reference value $AC_{ref}$ is updated based on the new setting of the amplitude of the current signal S1.

If the criteria are not met for any frequency, it may be determined that the criteria may not be met and the settings providing best results may be used. Thus, the adaptation may end with the setting of the amplitude, the gain and the frequency being updated 632 with values for which best results are obtained. Also, the AC reference value $AC_{ref}$ is updated based on the new setting of the amplitude of the current signal S1. However, if the DC level is still saturated or close to saturating, it may not be possible to extract meaningful information from the measured bioimpedance signal S2 and a new adaptation may be immediately triggered.

The adaptation of the bioimpedance signal acquisition according to the first embodiment discussed with reference to FIG. 5, may be useful in adapting the system 100 when a posture change has occurred. A posture change may significantly change conditions in which the bioimpedance signal is acquired and using the present settings as starting point for adaptation may not be relevant. The adaptation of the bioimpedance signal acquisition according to the second embodiment discussed with reference to FIG. 6, may be useful in adapting the system 100 when the signal drifts out of an acceptable range. Then, only a small change in parameter values may be needed and the adaptation according to the second embodiment may very quickly terminate with updated settings.

Thus, a system 100 may make use of both embodiments and may choose which adaptation process to be used based on further input. Such further input may be input indicating that a posture change has occurred or determining that a sudden large change in the AC and/or DC level has occurred.

However, it should be realized that the determining which of the first and second embodiments of adaptation of the bioimpedance signal acquisition should be used may be based on other conditions. Also, the system 100 may be set up to use only one of the embodiments.

Figure 7:
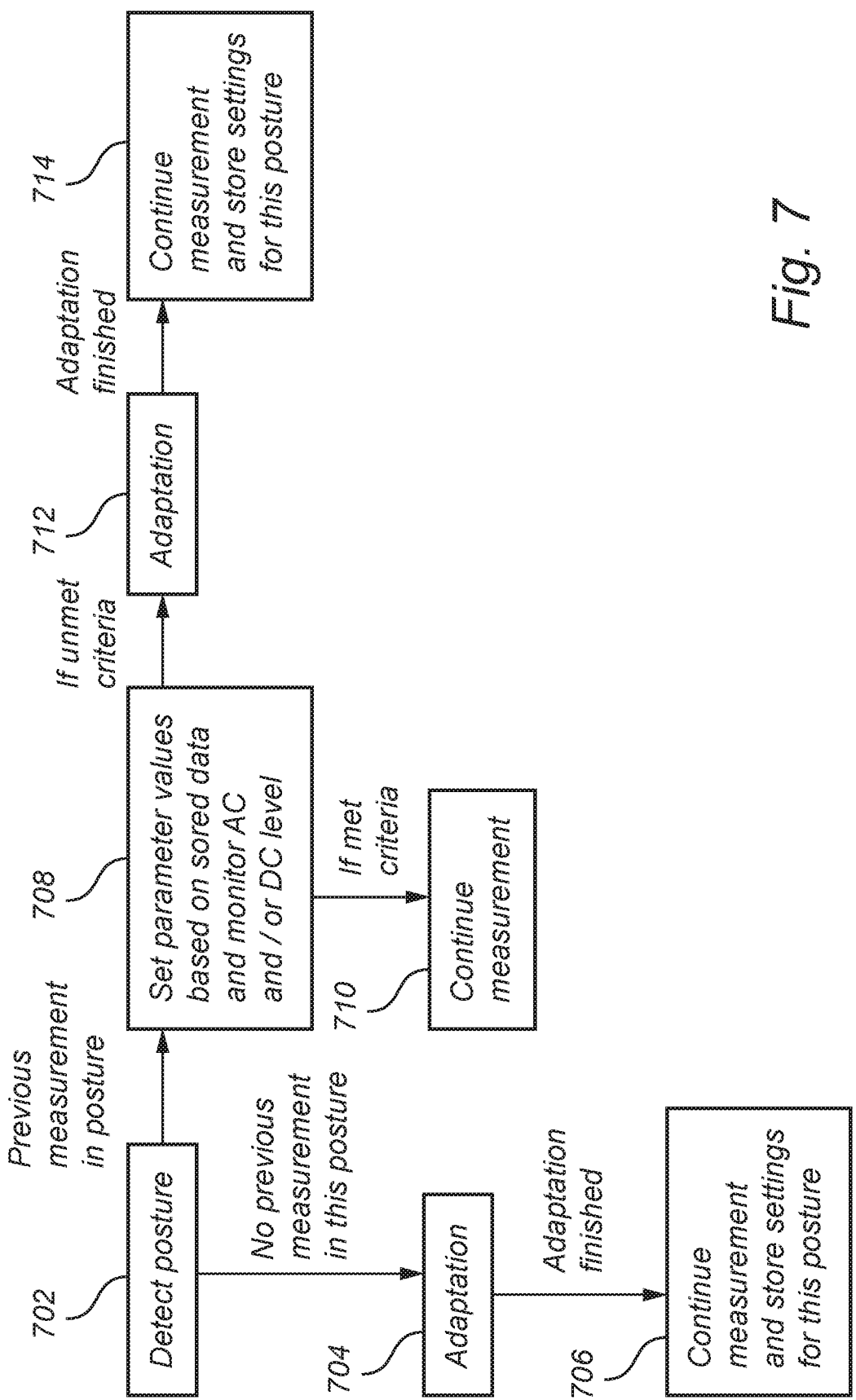
FIG. 7 is a schematic view of a method of adapting bioimpedance signal acquisition based on detection of posture of a subject, according to an example embodiment.

Referring now to FIG. 7, an embodiment of adaptation of the bioimpedance signal acquisition in relation to a posture change will be described.

The adaptation is based on input of a posture of the subject. Thus, as described above, the posture detection module 50 is used for determining the posture of the subject.

When a new posture is detected 702 by the posture detection module, the adaptation may be started. First, the posture may be determined. Here, the posture is denoted i.

Then, it is determined whether a previous measurement of the bioimpedance signal has been done for the posture i, either during calibration or during previous measurements. If no previous measurements have been done, no calibration data for the posture i may be stored. Thus, an adaptation is made 704 either according to the first embodiment as discussed in relation to FIG. 5 or according to the second embodiment as discussed in relation to FIG. 6.

When the adaptation is finished, the bioimpedance signal acquisition may be continued 706 using the determined settings. Further, the settings of the amplitude and frequency of the current signal and the gain of the bioimpedance signal measurement module 20 may be stored in relation to the posture i. Thus, the settings may be later retrieved, if the subject again assumes the same posture i.

If it is found when a new posture i is detected 702 that previous measurements have been done for the posture i, stored data applying to the posture i may be retrieved. Then, the current amplitude and frequency and the gain may be set 708 using the retrieved values. The stored data may be calibration data generated during calibration of the system 100. However, when measurements are made in a posture i, the calibration data may be updated with the last settings used with the subject being in the posture.

Once the retrieved settings have been set, the AC and/or DC levels may be monitored in order to determine whether data quality is acceptable. In this respect, the AC level may be compared to an AC reference value range based on an AC reference value for the posture settings for the posture i, $AC_{ref,i}$.

If the criteria are met, the bioimpedance signal is acquired with acceptable data quality and measurement of the bioimpedance signal may continue 710 using the settings for the parameters.

If the criteria are not met, an adaptation is made 712 either according to the first embodiment as discussed in relation to FIG. 5 or according to the second embodiment as discussed in relation to FIG. 6.

When the adaptation is finished, the bioimpedance signal acquisition may be continued 714 using the determined settings. Further, the settings of the amplitude and frequency of the current signal and the gain of the bioimpedance signal measurement module 20 may be stored in relation to the posture i. Thus, the updated settings may be later retrieved, if the subject again assumes the same posture i.

In the above, adaptation of the bioimpedance signal acquisition has mainly been discussed using the amplitude of the current signal S1, the frequency of the current signal S1 and the gain of the measured bioimpedance signal S2. However, adaptation of the bioimpedance signal acquisition may alternatively or additionally use selection of which electrodes 70 to be included for measuring the bioimpedance signal.

According to one embodiment, selection of electrodes 70 may be performed during set-up of the system 100. Thus, the electrodes 70 to be used may be selected based on subject characteristics, such as gender and BMI, and on a position of the electrodes 70 on the subject (such as positioning or orientation on chest). Hence, the electrodes 70 to be used may be pre-selected and the same electrode pair(s) may be used throughout a session of bioimpedance signal acquisition.

According to a second embodiment, selection of electrodes 70 may be based on a calibration performed during set-up of the system 100. Thus, the electrode pair(s) may be selected based on measurements of which electrodes 70 that provide a highest AC level of the measured bioimpedance signal S2. Then, the selected electrodes 70 may be used throughout a session of bioimpedance signal acquisition.

According to a third embodiment, selection of electrodes 70 may be included both in a calibration process and in an adaptation process. Thus, the selection of electrodes 70 may be included as a last step after the parameter values of amplitude and frequency of the current signal S1 and gain of the measured bioimpedance signal S2 have been varied. Thus, if the criteria are not met, the selection of electrodes 70 may be varied for different configurations of electrodes 70 and the settings of the amplitude, gain and frequency may be swept in order to find settings.

Figure 8:
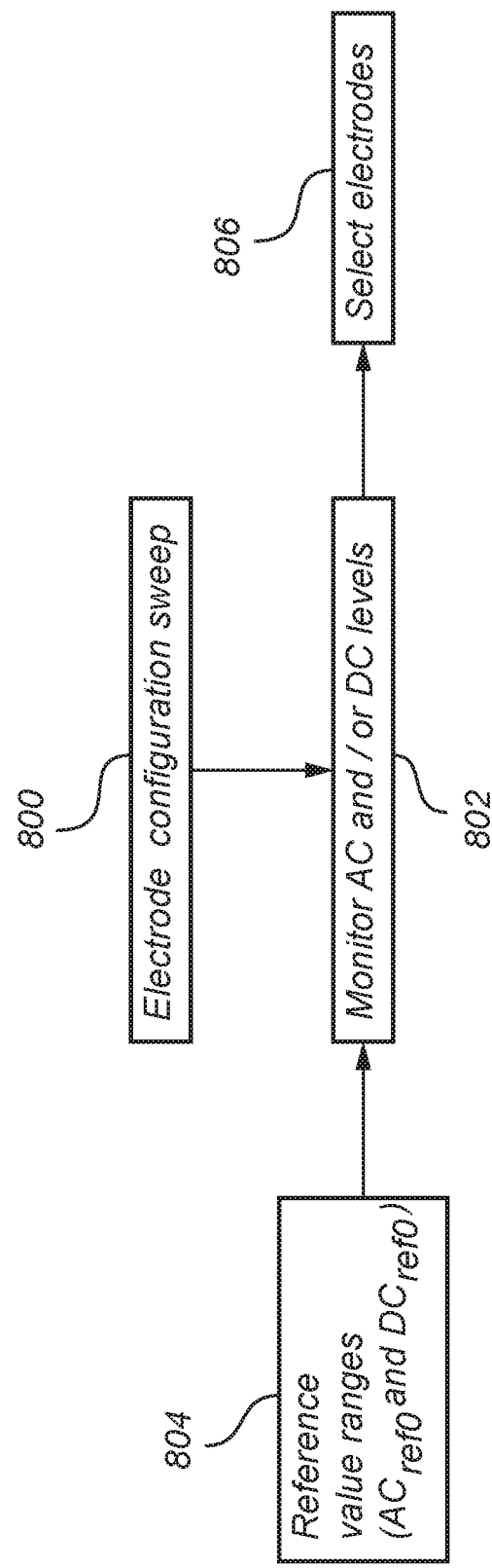
FIG. 8 is a schematic view of a method of adapting bioimpedance signal acquisition based on selecting electrodes to be used, according to an example embodiment.

Referring to FIG. 8, selection of electrodes 70, which may be used in the second or third embodiment, is discussed in further detail.

The electrode configuration is swept 800. If a two-electrode measurement is used, i.e. the same electrodes 70 are used both for injecting the current signal S1 and sensing the voltage generated by the current signal S1, the pair of electrodes 70 to be used may be varied starting with the electrodes 70 being farthest away from each other towards the electrodes 70 being closest to each other.

For each electrode pair, the amplitude of the current signal S1, the gain of the measured bioimpedance signal S2 and the frequency of the current signal S1 may be swept. During sweeping of the amplitude of the current signal S1, the measured bioimpedance signal S2 is acquired for each setting. The AC level and/or DC level of the measured bioimpedance signal S2 is monitored 802. The AC reference value range and/or the DC reference value range may be provided 804 as input to the monitoring of the AC and/or DC levels, or single values $AC_{ref,0}$ and $DC_{ref,0}$ may be provided as input allowing forming of the AC reference value range and the DC reference value range.

If the criterion or criteria are met, the adaptation may be terminated and settings of the parameters including the electrodes 70 to be included in the electrode pair may be selected 806 based on highest AC level of the signal. If the criterion or criteria are met, all possible electrode pairs need not be checked, but rather the electrodes 70 for which the criterion or criteria are met may be selected.

The process of selecting electrodes 70 may also be performed in relation to a maximum time. Thus, a maximum time may be set, such that parameter modification may not continue for a time period exceeding the maximum time. Thus, if the adaptation process has not terminated within the maximum time, the settings providing best results may be used.

If a four-electrode measurement is used, i.e. two electrodes 70 are used for injecting the current signal S1 and two other electrodes 70 are used for sensing the voltage generated by the current signal S1, the electrode sweep may start with two outer electrodes 70 having the largest distance between them for applying the current signal S1 to the subject in combination with two inner electrodes 70, arranged between the two outer electrodes 70 and having the largest distance between them for sensing the generated voltage.

For instance, if a row of six electrodes 70 are provided and the electrodes are numbered 1-6 along the row, the electrode sweep may start by using electrodes 1 and 6 for current signal injection and electrodes 2 and 5 for voltage sensing. Then, a combination of electrodes 1 and 6 for current signal injection and electrodes 3 and 4 for voltage sensing may be tested. Finally, a combination of electrodes 2 and 5 for current signal injection and electrodes 3 and 4 for voltage sensing may be tested. If none of these set-ups provide a bioimpedance signal of acceptable quality, a combination of electrodes 1 and 4 for current signal injection and electrodes 2 and 3 for voltage sensing may be tested followed by a combination of electrodes 3 and 6 for current signal injection and electrodes 4 and 5 for voltage sensing.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. An electronic system for bioimpedance signal acquisition, comprising:

a current signal injection module configured to generate a current signal to be applied to a subject;

a bioimpedance signal measurement module configured to measure, via a plurality of electrodes, a bioimpedance signal based on a voltage generated by the current signal applied to the subject;

a data quality detection module configured to detect one or more of an AC level and a DC level of the measured bioimpedance signal and to determine whether the one or more levels of the measured bioimpedance signal are within or outside a respective AC reference value range and a DC reference value range; and a signal adaptation module configured to control the bioimpedance signal measurement module to select an electrode pair of the plurality of electrodes, separated by a distance, based on the detection of whether the one or more levels of the measured bioimpedance signal are within or outside the one or more respective reference value ranges to facilitate modification of a plurality of parameters of the current signal injection module or the bioimpedance signal measurement module, wherein when the detected one or more levels of the measured bioimpedance signal is below the one or more respective reference value ranges, the signal adaptation module is configured to control the bioimpedance signal measurement module to increase the distance between electrode pairs by selecting an electrode pair having a distance therebetween that is greater than a distance between a currently selected electrode pair to thereby increase the amplitude of the bioimpedance signal, and when the detected one or more levels of the measured bioimpedance signal is above the one or more respective reference value ranges, the signal adaptation module is configured to control the bioimpedance signal measurement module to decrease the distance between electrode pairs by selecting an electrode pair having a distance therebetween that is lower than a distance between a currently selected electrode pair to thereby decrease the amplitude of the bioimpedance signal, and wherein the signal adaptation module is configured to adjust parameters that specify an amplitude of the current signal, a frequency of the current signal, and a gain of the bioimpedance signal measurement module to bring the AC level and the DC level within the AC reference value range and DC reference value range, respectively.

2. The system for bioimpedance signal acquisition according to claim 1, wherein the AC reference value range and the DC reference value range are predefined value ranges, value ranges defined by performing a system calibration, or value ranges defined by performing a parameter modification by the signal adaptation module.

3. The system for bioimpedance signal acquisition according to claim 1, wherein the AC reference value range relates to changes in bioimpedance due to respiration and the DC reference value range relates to a change in DC level of the bioimpedance signal measurement module.

4. The system for bioimpedance signal acquisition according to claim 1, wherein the data quality detection module is configured to communicate a control signal to the signal adaptation module when the one or more levels of the measured bioimpedance signal is within or outside the reference value range.

5. The system for bioimpedance signal acquisition according to claim 4, wherein the signal adaptation module is configured to start and stop modifying at least one parameter of the current signal injection module or the bioimpedance signal measurement module responsive to the control signal.

6. The system for bioimpedance signal acquisition according to claim 4, wherein the data quality detection module is configured to detect the subject's respiratory event before sending the control signal to the signal adaptation module to start parameter modification.

7. The system for bioimpedance signal acquisition according to claim 1, wherein the data quality detection module is configured to monitor the one or more levels of the measured bioimpedance signal continuously or at predetermined time intervals.

8. The system for bioimpedance signal acquisition according to claim 1, further comprising a posture detection module configured to detect a posture of the subject, wherein the data quality detection module is configured to monitor the one or more levels of the measured bioimpedance signal when a posture change is detected by the posture detection module.

9. The system for bioimpedance signal acquisition according to claim 8, wherein the signal adaptation module is configured to modify at least one parameter of the current signal injection module or the bioimpedance signal measurement module further based on posture information from the posture detection module.

10. The system for bioimpedance signal acquisition according to claim 8, wherein settings for at least one parameter of the current signal injection module or the bioimpedance signal measurement module are determined for a subject for different postures of the subject and the determined settings are stored for re-using the at least one parameter as initial settings when a posture change is detected by the posture detection module.

11. A wearable device for biosignal acquisition comprising a system for bioimpedance signal acquisition according to claim 1.

12. A method for bioimpedance signal acquisition comprising, in an electronic system according to claim 1:
generating a current signal;
applying the current signal to a subject;
measuring, via a first electrode pair of the bioimpedance signal measurement module, a bioimpedance signal based on a voltage generated by the current signal applied to the subject;
detecting one or more of an AC level and a DC level of the measured bioimpedance signal to thereby determine whether the one or more levels of the measured bioimpedance signal are within or outside of one or more of an AC reference value range and a DC reference value range, respectively; and
selecting a different electrode pair of the plurality of electrodes based on whether the one or more levels of the measured bioimpedance signal are within or outside the one or more respective reference value ranges to facilitate modification of at least one parameter of the current signal injection module or the bioimpedance signal measurement module.

13. A tangible, non-transitory computer-readable media comprising instructions encoded therein, wherein the instructions, when executed by one or more processors, cause an electronic system according to claim 1 to perform a method comprising:
generating a current signal;
applying the current signal to a subject;

measuring, via a first electrode pair of the bioimpedance signal measurement module, a bioimpedance signal based on a voltage generated by the current signal applied to the subject;

detecting one or more of an AC level and a DC level of the measured bioimpedance signal to thereby determine whether one or more levels of the measured bioimpedance signal are within or outside an AC reference value range and a DC reference value range, respectively; and selecting a different electrode pair of the plurality of electrodes based on whether the one or more levels of the measured bioimpedance signal are within or outside the one or more respective reference value ranges to facilitate modification of at least one parameter of the current signal injection module or the bioimpedance signal measurement module.

14. The electronic system according to claim 1, wherein the parameters are configured to be individually adjusted, wherein if after adjustment of a first parameter, one of the AC level and the DC level is still not within the AC reference value range and the DC reference value range, respectively, a second parameter is adjusted, and if after adjustment of the second parameter, one of the AC level and the DC level is still not within the AC reference value range and the DC reference value range, respectively, a third parameter is adjusted.

* * * * *